(12) United States Patent
Sample et al.

(10) Patent No.: US 8,523,859 B2
(45) Date of Patent: Sep. 3, 2013

(54) VACUUM-ASSISTED WOUND HEALING AROUND A PIN-SITE

(75) Inventors: Whitney Sample, Wilmington, DE (US); J. Richard Bowen, Wilmington, DE (US); Tariq Rahman, Moylan, PA (US)

(73) Assignee: The Nemours Foundation, Jacksonville, FL (US)

( * ) Notice: Subject to any disclaimer, the term of this patent is extended or adjusted under 35 U.S.C. 154(b) by 1362 days.

(21) Appl. No.: 11/497,916

(22) Filed: Aug. 2, 2006

(65) Prior Publication Data

US 2008/0051828 A1 Feb. 28, 2008

(51) Int. Cl.
*A61B 17/08* (2006.01)

(52) U.S. Cl.
USPC .......................................... 606/59; 606/213

(58) Field of Classification Search
USPC ............... 604/73, 75, 213; 623/213, 215; 11/73–76, 213; 602/42–53; 606/53–59
See application file for complete search history.

(56) References Cited

U.S. PATENT DOCUMENTS

| | | | | |
|---|---|---|---|---|
| 4,675,006 A | | 6/1987 | Hrushesky | 604/180 |
| 4,856,504 A | * | 8/1989 | Yamamoto et al. | 606/59 |
| 4,915,694 A | | 4/1990 | Yamamoto et al. | 604/180 |
| 5,000,741 A | | 3/1991 | Kalt | 604/180 |
| 5,080,661 A | | 1/1992 | Lavender et al. | 606/54 |
| 5,211,639 A | | 5/1993 | Wilk | 604/317 |
| 5,470,321 A | * | 11/1995 | Forster et al. | 604/174 |
| 5,478,333 A | | 12/1995 | Asherman, Jr. | 604/304 |
| 5,507,749 A | * | 4/1996 | Draenert | 606/94 |
| 5,540,675 A | | 7/1996 | Hasson | 606/1 |
| 5,549,584 A | | 8/1996 | Gross | 604/313 |
| 5,569,207 A | | 10/1996 | Gisselberg et al. | 604/175 |
| 5,636,643 A | | 6/1997 | Argenta et al. | 128/897 |
| 5,645,081 A | * | 7/1997 | Argenta et al. | 128/897 |
| 5,662,625 A | | 9/1997 | Westwood | 604/305 |
| 5,725,553 A | | 3/1998 | Moenning | 606/213 |
| 5,735,833 A | * | 4/1998 | Olson | 604/289 |
| 5,810,795 A | | 9/1998 | Westwood | 604/305 |
| 5,833,666 A | * | 11/1998 | Davis et al. | 604/180 |
| 5,941,859 A | * | 8/1999 | Lerman | 604/289 |
| 6,032,672 A | | 3/2000 | Taylor | 128/898 |
| 6,179,804 B1 | * | 1/2001 | Satterfield | 604/23 |
| 6,214,012 B1 | * | 4/2001 | Karpman et al. | 606/93 |
| 6,402,724 B1 | * | 6/2002 | Smith et al. | 604/289 |
| 6,471,685 B1 | | 10/2002 | Johnson | 604/890.1 |
| 6,553,998 B2 | * | 4/2003 | Heaton et al. | 128/897 |
| 6,626,891 B2 | | 9/2003 | Ohmstede | 604/543 |
| 6,682,506 B1 | | 1/2004 | Navarro | 604/174 |
| 6,695,823 B1 | | 2/2004 | Lina et al. | 604/304 |
| 6,767,334 B1 | | 7/2004 | Randolph | 604/35 |
| 6,856,821 B2 | | 2/2005 | Johnson | 600/345 |
| 6,863,674 B2 | | 3/2005 | Kasahara et al. | 606/108 |
| 7,022,113 B2 | * | 4/2006 | Lockwood et al. | 604/313 |

(Continued)

*Primary Examiner* — Kevin T Truong
*Assistant Examiner* — Christopher Beccia
(74) *Attorney, Agent, or Firm* — Drinker Biddle & Reath LLP

(57) ABSTRACT

A vacuum-assisted wound healing device is provided comprising an airtight hollow conical member surrounding a skin-breaching bone stabilization device, and a port for attaching a suction tube. The conical member has an opening at one end conforming to the circumference of the shaft of a bone stabilization device, and a opening at the other end to enclose a wound in a patient's skin surrounding the bone stabilization device. The device may be used to provide controlled reduced pressure to the wound site, reducing healing time and risk of infection.

5 Claims, 3 Drawing Sheets

(56) References Cited

U.S. PATENT DOCUMENTS

| | | | |
|---|---|---|---|
| 7,216,651 B2* | 5/2007 | Argenta et al. | 128/897 |
| 7,338,482 B2* | 3/2008 | Lockwood et al. | 604/543 |
| 7,361,184 B2* | 4/2008 | Joshi | 606/213 |
| 2001/0029956 A1 | 10/2001 | Argenta et al. | 128/897 |
| 2004/0122434 A1* | 6/2004 | Argenta et al. | 606/86 |
| 2005/0261642 A1* | 11/2005 | Weston | 604/313 |
| 2008/0051828 A1* | 2/2008 | Sample et al. | 606/213 |
| 2008/0281324 A1* | 11/2008 | Webb et al. | 606/59 |

* cited by examiner

VACUUM-ASSISTED WOUND HEALING AROUND A PIN-SITE

FIELD OF THE INVENTION

This invention relates to wound therapy. In particular, it provides a device and method for applying vacuum-assisted wound therapy.

BACKGROUND OF THE INVENTION

There are many orthopedic procedures that involve placing pins or screws into bone. External skeletal fixation involves stabilization of fractured bone segment by pins or screws which protrude through the overlying skin. The pins or screws may be connected to an external frame for stabilization. These external skeletal fixation appliances comprise swivel joints, connecting bars, sliding bars, articulations, and anchorage clamps intended to hold and position transcutaneous pins. For example, when a patient suffers a severe bone injury or undergoes limb-lengthening surgery, it is often necessary to stabilize the fracture area with an external fixation device.

Often, the transcutaneous pins or screws of an external fixation device must remain in place for an extended period. These appliances create a breach in the skin. Because of this breach, the resulting pin-site wound provides a path along which microorganisms present on the skin surface may move into deeper tissues. In addition, inflammation and localized edema at the wound site may lead to a loss of blood flow to the surrounding tissue, decreasing the tissue's ability to fend off infection and slowing the healing process.

The antiseptic effect of vacuum therapy is well-known. Maintaining vacuum pressure on the area around a wound site not only inhibits microbe migration to the wound, it also quickly reduces bacteria population and reproduction in the wound area. Vacuum-assisted wound dressings may comprise a thin film semi-permeable cover containing a perimeter adhesive for creating an air tight seal with the skin. A vacuum tube penetrates the cover. Such dressings are difficult to apply however, where a bone stabilization pin or screw extends through the skin. The vacuum supplied under the cover tends to collapse the thin film cover onto the skin. If used with a protruding pin, the film would tend to tent around the top of pin, and apply an unwanted destabilizing force to the pin.

An alternative vacuum device is disclosed in Argenta et al. (U.S. Pat. No. 5,636,643). Argenta discloses a wound cover that is either rigid or semi-rigid and which has a port for attachment to a vacuum source. The cover fits over the wound and is sealed against the surrounding skin to maintain the vacuum. The device is adapted for use over large open wounds such as burns, pressure sores, and wounds requiring skin grafts or flaps. While a protruding stabilization pin could conceivably be entirely captured within the dome of the rigid cover, the cover is a rather large and unwieldy device and may not be suitable for covering the small wound surrounding a pin. Similarly, such a device would not be suitable for situations in which several pins are used and connected to a common rack or brace, such as in the case of a badly shattered bone. There is also the risk that an external force could cause the pin to rupture the cover.

Yamamoto et al. (U.S. Pat. Nos. 4,856,504 and 4,915,694) disclose antimicrobial wound dressings and skin fixators suitable for use with orthopedic pins and percutaneous conduits (such as catheters), respectively. These devices comprise antimicrobial pads adapted to fit closely to the skin around a pin or conduit. The pad is then covered by a flange with an orthogonally projecting collar which fits around the pin and fits flush with and covers the antimicrobial pad. These devices are aimed at preventing infection around the wound in the patient's skin through use of traditional antiseptic medications and do not contemplate the use of vacuum-assisted healing techniques.

It is therefore apparent that a need exists for a device that can conveniently apply vacuum-assisted treatment to pin-site wounds.

SUMMARY OF THE INVENTION

In accordance with the present invention, a device is provided for applying therapeutic vacuum to a wound surrounding the shaft of a bone stabilization device that extends through the skin of a patient. By "bone stabilization device" is meant a transcutaneous element, such as a pin or screw, which is adapted for embedding in the bone of the patient and extending through the skin. The device of the invention comprises a hollow generally conical member defining an enclosed space through which the stabilization device may pass. The conical member has at a first end a first opening adapted to conform to the bone stabilization shaft. At an opposite second end, the device has a second opening adapted to enclose a wound in the skin surrounding the bone stabilization device shaft. The openings are dimensioned, respectively, for conforming to the bone stabilization device shaft, and for enclosing the wound surrounding the bone stabilization device shaft. The opening for enclosing the wound will typically be larger than the opening conforming to the bone stabilization device. The conical member has, preferably at a point intermediate the ends thereof, a port for connecting a suction tube to the conical member, to communicate a negative pressure from a vacuum source to a space defined by the conical member. The conical member has sufficient flexibility at the first end to contract against the bone stabilization device shaft to form an airtight seal therewith.

In one embodiment, the conical member has sufficient rigidity to generally maintain its conical shape and resist collapsing on to the wound during use. In another embodiment, an antimicrobial sponge or other soft object is placed between the conical member and the wound, and the conical member has sufficient flexibility to partially collapse onto the antimicrobial sponge.

One embodiment the device of the invention includes a sealable slit in the conical member extending from the conical member first and second openings. The slit facilitates placement of the device around a pin and wound site. A sealing device, such as a flexible adhesive tape, is used to close the slit. While use of a flexible adhesive for sealing the slit is contemplated, the slit may be closed and sealed by any means that will serve to maintain the integrity of the seal created by the mating of the structure to the skin and the stabilization device.

A method for applying a vacuum to a wound surrounding the shaft of a bone stabilization device that extends through the skin is provided, comprising, placing the device of the invention over a wound and a protruding bone stabilization device shaft such that the shaft passes through both openings of the conical member to enclose the wound, connecting the device to a vacuum source, and applying vacuum pressure to the device.

Although these Figures depict an embodiment of the contemplated invention, they should not be construed as foreclosing alternative or equivalent embodiments readily apparent to those of ordinary skill in the subject art.

DETAILED DESCRIPTION OF THE PREFERRED EMBODIMENTS

Figure 1:
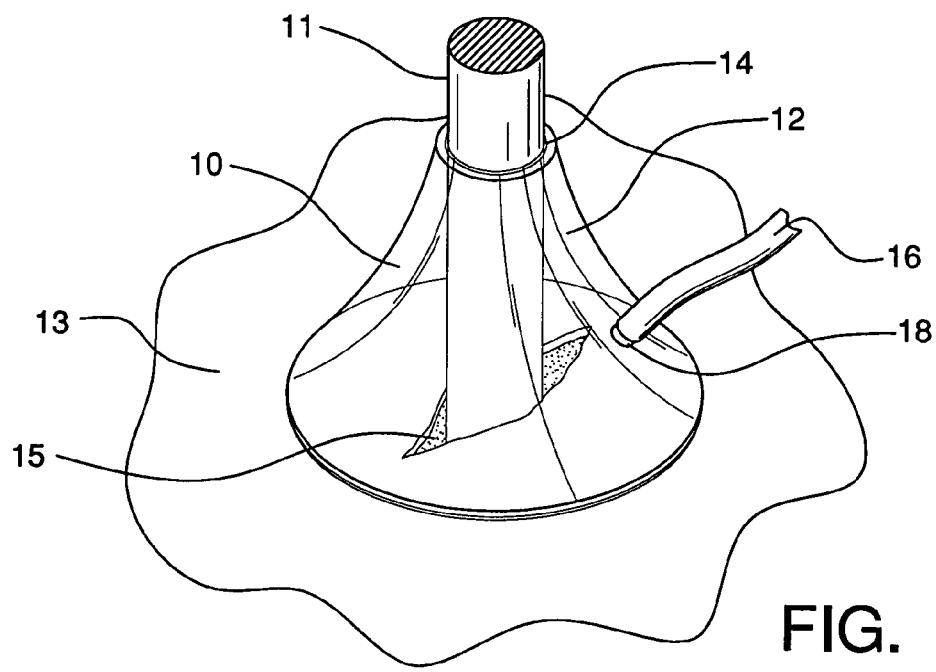
FIG. 1 shows a perspective view of a wound treatment device for applying therapeutic vacuum to a wound surrounding the shaft of a bone stabilization device that extends through a patient's skin.

As shown in FIG. 1, a wound treatment device 10 is provided for applying a therapeutic vacuum for treating a wound 15 caused by a bone stabilization device 11 that protrudes through a patient's skin 13. In the embodiment shown in FIG. 1, the device 10 includes a hollow, preferably generally conical member 12. At one end, the conical member 12 has a small opening conforming to the shaft of the bone stabilization device 11. At the other and opposite end, the conical structure 12 has a larger opening that is dimensioned to enclose the wound 15 surrounding the bone stabilization device 11. While the openings in the generally conical member 12 will typically be circular, it is noted that other shape openings are possible. For example, the body of the conical member may be oval in cross-section, and the opening contacting the skin will be oval. Likewise, the shape of the opening for engaging the shaft of the bone stabilization device is advantageously selected to conform to the cross-sectional shape of the shaft, if other than circular.

It is also contemplated that the openings may not be predetermined, instead being defined by the attachment of the member 12 to the bone stabilization device 11. Thus, in the event that the stabilization device is rectangular, the upper opening would conform to the shape of the device upon application of negative pressure, as will become more apparent below.

Preferably, the conical member is comprised of a flexible, semi-rigid, airtight material so that when reduced pressure is applied, the walls of the conical member are drawn inwards toward the skin and stabilization device. In a preferred embodiment, the conical member is comprised of a flexible, semi-rigid polymer such as silicone or low linear density polyethylene. Ideally, the cone geometry is such that while the ends of the cone conform to the stabilization device and the skin respectively, the middle section of the cone is drawn inwards under the applied negative pressure. Use of a flexible but semi-rigid polymer in the conical member allows the structure to conform roughly to the surfaces of the stabilization device shaft and the patient's skin while also retaining its shape when the vacuum is applied. Whatever material is used, the conical member preferably has sufficient flexibility at the end having the smaller opening to contract against the stabilization device and form an air tight seal, but preferably has sufficient rigidity to generally maintain its conical shape and prevent the structure from collapsing onto the wound, as well as the ability to securely support the vacuum port and tube. The conical member should also have sufficient flexibility at the opposite end to form an airtight seal with the skin. The conical member 12 can be optionally secured to the stabilization device 11 and to the skin 13 by adhesive 14. Any suitable adhesive which can adhere to the skin can be used.

As shown in FIG. 1, the wound 15 is completely enclosed within the conical member 12. Negative pressure is supplied to the interior of the enclosure formed by the member through a tube 16. The tube 16 connects to the conical member 12 through a port 18 formed in the conical member 12, preferably at a location that is between the ends of the conical member. Tube 16 connects the port 18 to a vacuum source (not shown) which supplies a negative pressure (vacuum) to the space inside the conical member 12. The tube 16 may be either integrally connected to port 18, or it may be capable of attachment by any commonly understood or suitable means. In a preferred embodiment, the tube measures ¼ inch in diameter and is comprised of a flexible polymer such as polycarbonate, e.g. LEXAN® brand polycarbonate.

Figure 3A:
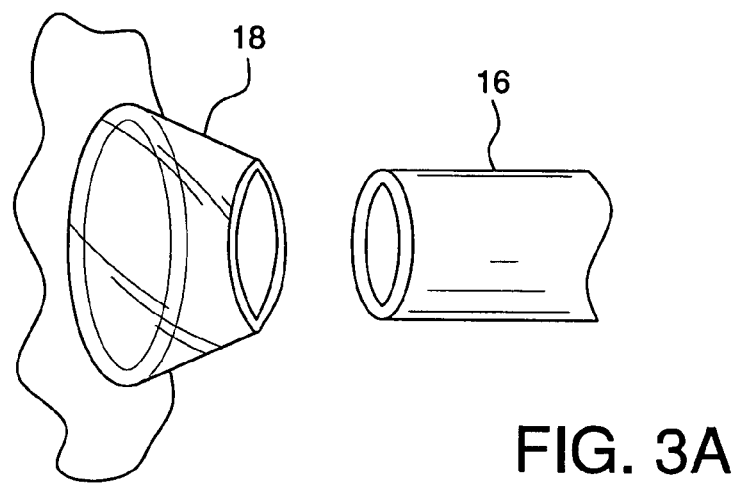
FIGS. 3A-3C show an enlarged perspective view of an alternate port design in three stages of operation—before insertion of the tube, with the tube inserted and withdrawing air, and after sealing.
Figure 3B:
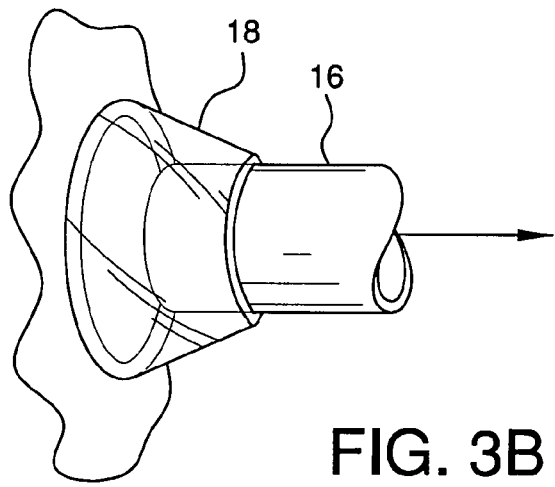
Figure 3C:
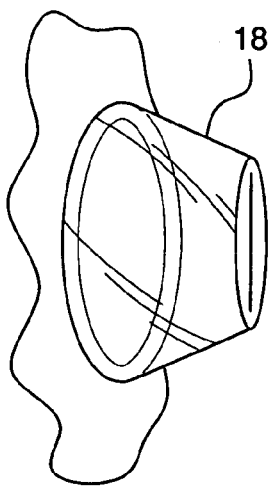

While the port 18 and tube 16 are both shown as cylindrical in shape, it is also contemplated that either or both can be formed in a variety of shapes. For example, referring to FIGS. 3A-3C, the port 18 can be formed from two flaps of material that extend from the member 12 and which flaps are attached at their upper and lower ends, thereby defining a narrow slit. The tube 18 can be easily inserted into the slit when a vacuum is needed. After sufficient negative pressure is applied to the enclosure, the flaps can then be closed, such as by clipping or taping, and the tube 18 removed.

The level and duration vacuum pressure necessary to achieve a suitable antiseptic effect is well understood in the art. In a preferred embodiment, the vacuum pressure applied is 5 in Hg below atmospheric pressure until the bacterial count is reduced to a desired level. Although not shown, a sensing device can be located along the tube for monitoring bacterial count. Alternately, when substantially all the air is withdrawn from the enclosure, the enclosure could be sealed.

Figure 2:
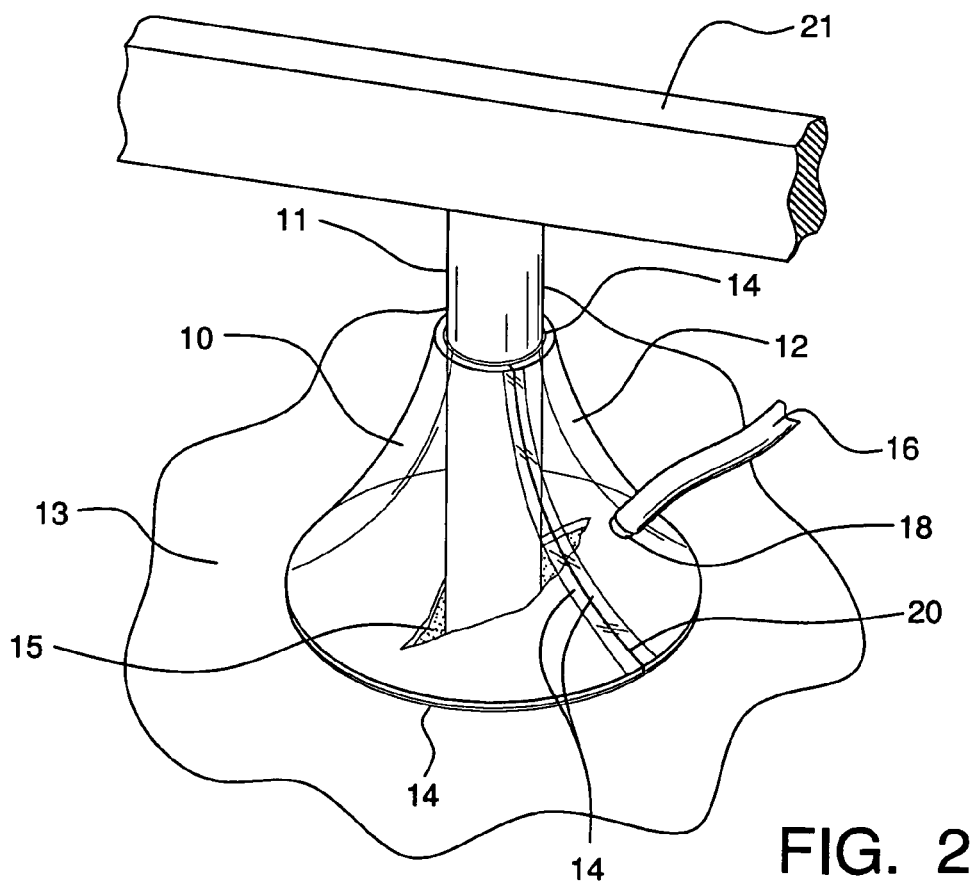
FIG. 2 shows a perspective view of an alternative embodiment of a wound treatment device for applying therapeutic vacuum to a wound surrounding the shaft of a bone stabilization device that extends through a patient's skin.

As shown in FIG. 2, an alternative form of the device of the invention includes a slit 20 in the member which extends from one end to the other. This allows the device to be opened to fit around the shaft of a bone stabilization device which has already been inserted into the body of the patient, where access to the end of the stabilization device is blocked, for example, by a bar, rack, brace or frame or other structure, as shown in FIG. 2. The slit is then sealed, preferably by means of flexible adhesive material, such as adhesive tape or glue 14. This method of attachment enables the device to be used when the stabilization device is itself attached to a larger apparatus, such as in the case of a badly shattered bone where a series of pins or screws may be attached to a rack or brace 21. It should be readily apparent that the shape of the member 12 in this embodiment need not be conical before application of pressure. Instead, the member 12 may be formed from flexible material that has a flat sheet with a square, trapezoidal, or other shape. The sheet is wrapped around the pin and sealed to the pin and the skin, thus defining the conical shape.

The embodiment of the device of the invention shown in FIG. 1 may be fitted to the patient by passing the bone stabilization device shaft axially through the openings in the conical member until the larger opening contacts the patient's skin. Where the protruding end of the bone stabilization device is connected to a rack or frame, the alternative embodiment of the device of the invention, as shown in FIG. 2, is preferably employed. The stabilization device shaft passes through the slit in the conical member until the shaft extends through each opening in the conical member. The vacuum pressure is applied at either a constant or cyclical rate and for a time period sufficient to achieve the desired antiseptic effect as understood by those of ordinary skill in the art.

Figure 4:
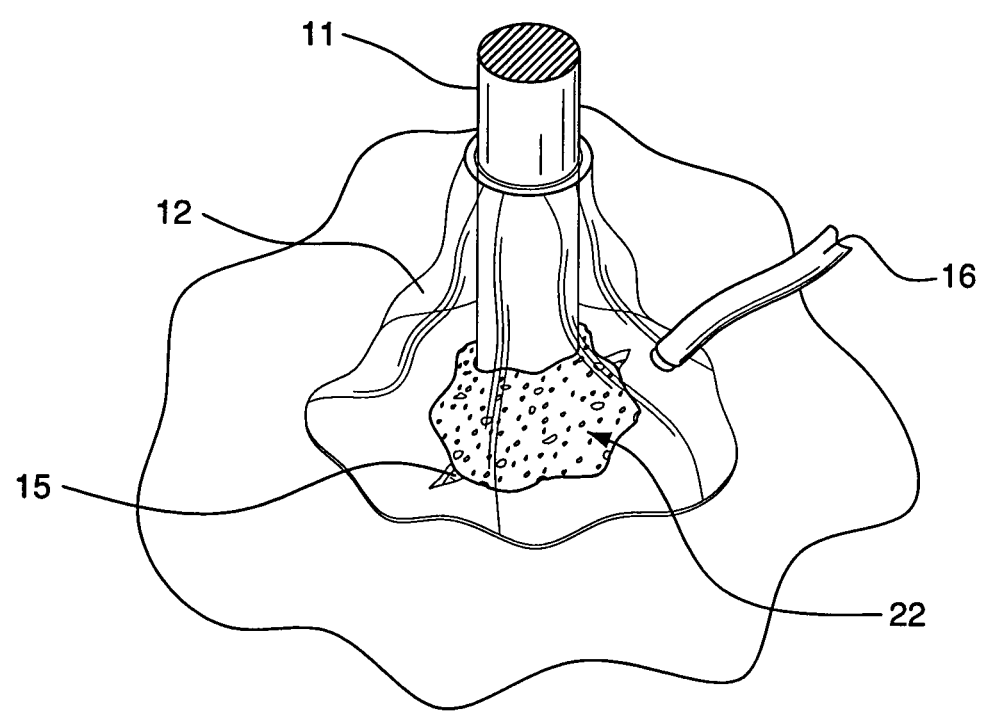
FIG. 4 shows a perspective view of a further alternative embodiment of a wound treatment device for applying therapeutic vacuum to a wound surrounding the shaft of a bone stabilization device that extends through a patient's skin.

As shown in FIG. 4, an alternative form of the device of the invention includes a conical member 12 that is sufficiently flexible to collapse under the pressure difference between external ambient pressure and the negative pressure inside the conical member. To protect the wound 15, a soft element 22, which may be a sponge, is placed between the conical member 12 and the wound. The soft element 22 may be treated with an antimicrobial substance. The antimicrobial sponge may be supplied in a package with the conical member 12 when the wound treatment device is supplied, or may be provided separately and combined with the conical member only when the wound treatment device 10 is applied to a patient. In some circumstances, the mechanical contact between the soft element 22 and the wound 15, where gentle mechanical forces are transmitted to the wound from the conical member 12 through the soft element 22, may mechanically stimulate the wound in such a manner as to promote healing. The use of the flexible conical member 12 without the soft element 22 is possible but in most circumstances less preferred.

All references cited herein are incorporated by reference. The present invention may be embodied in other specific forms without departing from the spirit or essential attributes thereof.

For example, although distinct embodiments have been described and shown in the several drawings, features from the different embodiments may be combined in a single embodiment. For example, the treatment device 10 shown in FIG. 4 may have either the connector 18 shown in FIG. 1 or the connector shown in FIGS. 3A to 3C. For example, the treatment device 10 shown in FIG. 4 may have a conical shape similar to that shown in FIG. 1 or may have the slit 20 shown in FIG. 2.

Accordingly, reference should be made to the appended claims, rather than to the foregoing specification, as indication the scope of the invention.

We claim:

1. A method of treating a wound surrounding the shaft of a bone stabilization device that protrudes through the skin of a patient comprising:

placing a device for applying therapeutic vacuum to a wound surrounding the shaft of a bone stabilization device that extends through the skin of a patient, comprising a hollow generally conical member having at a first end a first opening adapted to conform to the bone stabilization device shaft, and having at a second opposite end a second opening adapted to enclose a wound surrounding the bone stabilization device shaft, the conical member having, at a point between the ends thereof, a port for connecting a suction tube to the conical member to communicate a negative pressure from a vacuum source to a space defined by the conical member, the conical member having sufficient flexibility at the first end to form an airtight seal around the stabilization device shaft, over a wound and protruding bone stabilization device shaft such that the shaft passes through both openings in the conical member and the device encloses the wound;

connecting the vacuum tube to a source of vacuum; and applying vacuum pressure to the device.

2. The method of claim 1, wherein the applied vacuum pressure is constant.

3. The method of claim 1, wherein the applied vacuum pressure is cyclical.

4. The method of claim 1, wherein the edge of the second opening in the conical member is adhered to the skin of the patient with an adhesive.

5. The method of claim 1, wherein the edge of the first opening in the conical member is adhered to the shaft of the bone stabilization device with an adhesive.

* * * * *